United States Patent [19]

Wong

[11] Patent Number: 5,747,808
[45] Date of Patent: May 5, 1998

[54] NDIR GAS SENSOR

[75] Inventor: Jacob Y. Wong, Goleta, Calif.

[73] Assignee: Engelhard Sensor Technologies, Iselin, N.J.

[21] Appl. No.: 662,981

[22] Filed: Jun. 13, 1996

Related U.S. Application Data

[63] Continuation of Ser. No. 518,134, Aug. 22, 1995, abandoned, which is a continuation-in-part of Ser. No. 284,914, Aug. 2, 1994, Pat. No. 5,444,249, which is a continuation of Ser. No. 195,523, Feb. 14, 1994, abandoned.

[51] Int. Cl.$^6$ ..................................................... G01N 21/35
[52] U.S. Cl. .................. 250/343; 250/339.13; 356/437
[58] Field of Search ............................... 250/343, 344, 250/349, 338.4, 339.06, 339.13; 356/343, 432, 434, 437

[56] References Cited

U.S. PATENT DOCUMENTS

| | | | |
|---|---|---|---|
| 4,578,762 | 3/1986 | Wong | 364/497 |
| 4,694,173 | 9/1987 | Wong | 250/353 |
| 4,709,150 | 11/1987 | Burough et al. | |
| 5,055,688 | 10/1991 | Fabinski | 250/344 |
| 5,163,332 | 11/1992 | Wong | 73/863.33 |
| 5,255,072 | 10/1993 | Mikasa et al. | 356/432 |
| 5,265,470 | 11/1993 | Kaiser et al. | 73/178 R |

FOREIGN PATENT DOCUMENTS 9400750  1/1994  WIPO .................................. 356/437

OTHER PUBLICATIONS

Petersen, Kurt E., *Silicon as a Mechanical Material*, Proceedings of the IEEE, vol. 70, No. 5, May 1982, pp. 420–456.

Howe, Muller, Gabriel & Trimmer, *Silicon Micromechanics: sensors and actuators on a chip*, IEEE Spectrum, Jul. 1990, pp. 29–35.

Rosen, Jerome, *Machining In The Mirco Domain*, Mechanical Engineering, Mar. 1989, pp. 40–46.

Fraden, J., *AIP Handbook of Modern Sensors, Physics, Designs & Applications*, Chpt. 17 Chemical Sensors, pp. 545–546.

Wong, Jacob, *Performance Comparison Among Various Types Of Commercially Available Gas Sensors*, Gaztechnology, vol. 1, Apr. 1992, pp. 1–13.

The Infrared Information Analysis (IRIA) Center, Environmental Research Institute of Michigan, *The Infrared Handbook: Interference Filters, Optical Matters*, Chapter 7, at 103–137, (Wolfe, W., Zislis, G., rev. ed., 3d printing 1989).

*Primary Examiner*—Constantine Hannaher
*Attorney, Agent, or Firm*—Lyon & Lyon LLP

[57] ABSTRACT

A miniaturized NDIR gas sensor is manufactured using semiconductor micromachining techniques from a semiconductor material such as Si or GaAs. The NDIR gas sensor comprises an optical waveguide, a light source at one end of the waveguide, at least one light detector at the end of the waveguide opposite the light source, a diffusion type gas sample chamber formed within the waveguide and interposed in the optical path between the light source and light detector so that the light source and light detector are thermally isolated from the gas sample, and a separate bandpass filter interposed between the light source and each light detector. A miniaturized NDIR gas sensor is also provided in which the light source and light detector are located on the same end of the optical waveguide is also provided. Because the NDIR sensor is fabricated out of a semiconductor material, the source driver and signal processing electronics may be added directly to the sensor using integrated circuit fabrication techniques. Particles and smoke and dust may be kept out of the sample chamber by application of a gas permeable membrane over apertures in the sample chamber walls.

18 Claims, 8 Drawing Sheets

NDIR GAS SENSOR

This is a continuation of application Ser. No. 08/518,134, filed Aug. 22, 1995, now abandoned, which is a continuation-in-part of application Ser. No. 08/284,914, filed Aug. 2, 1994, now U.S. Pat. No. 5,444,249, which is a continuation of application Ser. No. 08/195,523, filed Feb. 14, 1994, now abandoned.

BACKGROUND OF THE INVENTION

1. Field of the Invention

The present invention generally relates to the field of gas sensing devices and, more particularly, to NDIR gas analyzers.

2. Description of the Prior Art

Nondispersive infrared (NDIR) gas analyzers are used for detecting the presence and concentration of various gases. The NDIR technique has long been considered one of the best methods for gas measurement. In addition to being highly specific, the NDIR gas analyzers are also very sensitive, stable and easy to maintain.

In contrast to NDIR gas sensors, which are by definition noninteractive, interactive optical gas sensors are less reliable, are generally nonspecific, and in some cases can be poisoned into a nonfunctional state.

Interactive gas sensors are generally nonspecific because the reagent being used to determine the concentration of the desired gas may react with other gases that are present. This will naturally result in false readings. Further, if the equilibrium of the reaction between the nonspecific gas and the reagent is such that the gas and reagent remain reacted even after the partial pressure of the gas drops in the environment being monitored, the sensor will no longer function properly and is poisoned.

The response time for NDIR gas sensors is also typically shorter than that for interactive gas sensors. The reason being that the kinetics of the reaction between the sample gas and reagent controls how quickly the sensor detects a change in the concentration of the gas in the environment being monitored.

Despite the fact that interactive gas sensors are unreliable and that the NDIR gas measurement technique is one of the best, NDIR gas analyzers have not enjoyed wide spread application because of their complexity and high cost of implementation.

In the past, NDIR gas analyzers typically included an infrared source, a motor-driven mechanical chopper to modulate the source, a pump to push or pull gas through a sample chamber, a narrow bandpass interference filter, a sensitive infrared detector plus expensive infrared optics and windows to focus the infrared energy from the source onto the detector.

In an attempt to reduce the cost and simplify the implementation of the NDIR technique, a low-cost NDIR gas sensor technique was developed. The low-cost NDIR technique employs a diffusion-type gas sample chamber of the type disclosed in U.S. Pat. No. 5,163,332, issued Nov. 17, 1992, to the present applicant, and hereby incorporated by reference. This diffusion-type gas sample chamber eliminates the need for: expensive optics, mechanical choppers, and a pump for pushing or pulling the gas into the sample chamber. As a result, a number of applications for the NDIR technique, which were previously considered impractical because of cost and complexity, have been opened.

The diffusion-type gas sample chamber of U.S. Pat. No. 5,163,332 uses an elongated hollow tube having an inwardly-facing specularly-reflective surface that permits the tube to function as a light-pipe for transmitting radiation from a source to a detector through the sample gas. A plurality of filtering apertures in the wall of the non-porous hollow tube permit the sample gas to enter and exit freely under ambient pressure. Particles of smoke and dust of a size greater than 0.1 micron are kept out of the chamber by use of a semi-permeable membrane that spans the apertures in the hollow tube, and condensation of the sample gas is prevented by heating the sample chamber electrically to a temperature above the dew point of the gas.

Although the low-cost NDIR gas sensor technique opened a wide variety of new applications, the gas sample chamber and the corresponding gas sensor of the low-cost NDIR technique are still too large for many potential gas sensor applications. As a result, applications in which low-cost NDIR gas sensors may be used remain limited. Furthermore, while the cost of gas sensors employing the gas sample chamber of U.S. Pat. No. 5,163,332 is less than previous NDIR gas sensors requiring expensive optics, pumps, and choppers, a further reduction in the cost of NDIR gas sensors would further increase the number of applications in which such sensors are used and the frequency of their use.

Therefore, while a need exists for a compact, inexpensive NDIR gas sensor, this need has gone unfilled. Accordingly, a goal of the present invention is to further advance the NDIR technique by providing a miniaturized, reliable, and low cost NDIR gas sensor.

SUMMARY OF THE INVENTION

The present invention is directed to an NDIR gas sensor for detecting the concentration of a predetermined gas. To this end, an optical waveguide is provided having a light source at one end and a light detector at the other end. A bandpass filter is interposed in the optical path between the light source and detector, so that the detector primarily receives radiation of a wavelength that is strongly absorbed by the gas whose concentration is to be determined. The waveguide is formed from two or more substrates of a semiconductor material, at least one of which has been micromachined. In addition, the light source and detector are directly manufactured on at least one of the semiconductor substrates used to form the optical waveguide. Preferably, a pair of windows are also optically disposed between the light source and detector so as to define therebetween a sample chamber within the optical waveguide. The windows thermally isolate the light source and light detector from the sample gas, thus preventing the sample gas from cooling these elements. The gas whose concentration is to be determined diffuses into and out of the sample chamber in the optical waveguide through apertures or slots in the semiconductor substrates.

Because the walls of the optical waveguide are reflective, radiation is transmitted from the light source to the light detector through the sample gas without the need for expensive optics. Furthermore, because gas sensors according to the present invention employ a diffusion-type gas sample chamber, no pump is required to push or pull the sample gas into the sample chamber.

In a preferred embodiment, a gas permeable dielectric layer is deposited over the apertures to act as a filter and prevent dust or smoke particles from entering the optical waveguide sample chamber. Preferably, the gas permeable layer prevents particles larger than about 0.1 μm from entering.

In another preferred embodiment, at least a portion of the optical waveguide is metallized thereby improving its internal reflectivity and the overall efficiency of the NDIR gas sensor according to the present invention.

In yet another preferred aspect of the present invention, an NDIR gas sensor is provided that prevents condensation of gases or vapors on the walls of the sample chamber. To accomplish this object, means are provided for heating the gas sample chamber so that its temperature remains above the dew point of any gas or vapor that might have a tendency to condense on an inner surface of the sample chamber.

Other integrated circuit semiconductor devices can also be added wherever needed to further enhance the performance of the NDIR gas sensor according to the present invention. For example, temperature sensors, pressure transducers, and humidity sensors may be added. In addition, a micro-flow sensor may be added to detect the flow rate of the sample gas through the sample chamber.

In a particularly preferred embodiment of the present invention, an NDIR gas sensor is provided which can be used to simultaneously determine the concentration of a plurality of gases in the gas sample. An NDIR gas sensor according to this embodiment is comprised of a plurality of detectors and a plurality of bandpass filters. Each bandpass filter is interposed in the optical path between the light source and one of the plurality of detectors. The number of gases whose concentration is desired to be determined dictates the specific number of detectors and bandpass filters that are required. Each bandpass filter, therefore, is designed so that the detector it is associated with primarily receives radiation of a wavelength that is strongly absorbed by the gas whose concentration that detector is to determine.

Alternatively, in this embodiment, at least one of the detectors may be used as a reference detector. In this situation, the bandpass filter interposed in the optical path between the light source and the reference detector must be designed to pass a neutral wavelength. In other words, the bandpass filter must pass a wavelength of light that is not absorbed by the gas sample.

In another particularly preferred embodiment, an NDIR gas sensor is provided wherein the light source and light detector are provided in a side by side relationship, both in optical communication with the opposite end of the optical waveguide, so that the sample chamber is interposed in the optical path between the two. An advantage of this relationship as opposed to an NDIR gas sensor which has a straight optical waveguide with a light source and a light detector provided at opposing ends is that the NDIR gas sensor of the present embodiment is twice as sensitive. Thus, the NDIR gas sensor of the present embodiment can achieve the same sensitivity with a sample chamber half as long.

In yet another preferred embodiment of the present invention, an optical waveguide is employed that includes a sample chamber that extends along an indirect path. As with the first embodiment, the light source and light detector are located at opposite ends of the waveguide and a pair of windows are preferably disposed between the light source and detector so as to define the sample chamber therebetween. Preferably the indirect path traversed by the sample chamber has a serpentine or spiral shape. An advantage of the present embodiment is that a sample chamber having a length much longer than the length of the substrate in which it is formed can be produced, thus providing enhanced sensitivity without substantially increasing the overall dimensions of the NDIR gas sensor.

Accordingly, it is a primary object of the present invention to provide a miniaturized NDIR gas sensor which is micromachined from a semiconductor material.

Further objects and advantages of the invention will be better understood from the following description considered in connection with accompanying drawings in which the preferred embodiments of the invention are illustrated by way of example. It is to be expressly understood, however, that the drawings are for the purpose of illustration and description only and are not intended as a definition of the limits of the invention.

DETAILED DESCRIPTION OF THE INVENTION

Figure 1:
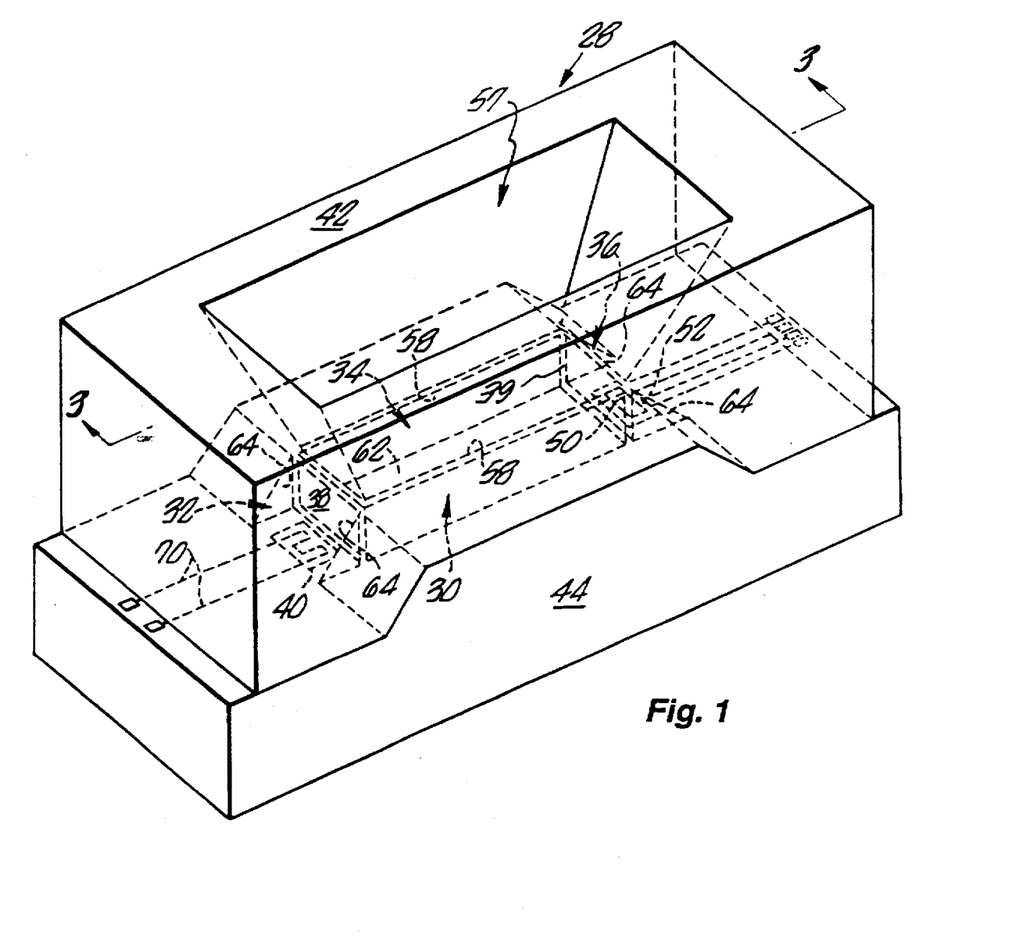
FIG. 1 is an oblique view of an NDIR gas sensor according to a first embodiment of the present invention.
Figure 2:
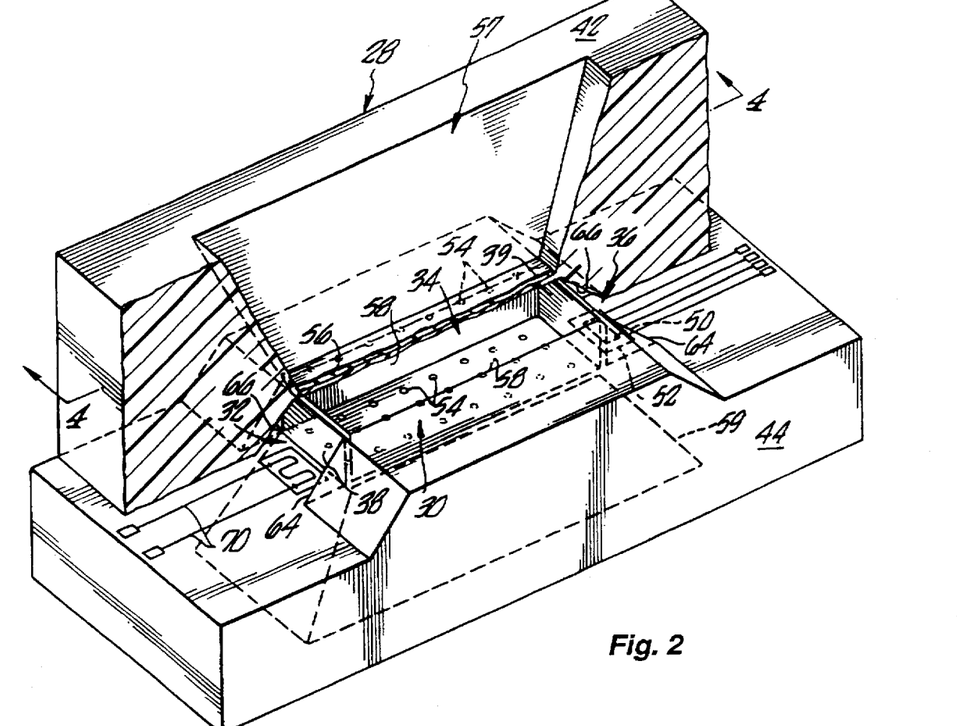
FIG. 2 is a an oblique view showing a partial cutaway of an NDIR gas sensor according to a first embodiment of the present invention.
Figure 3:
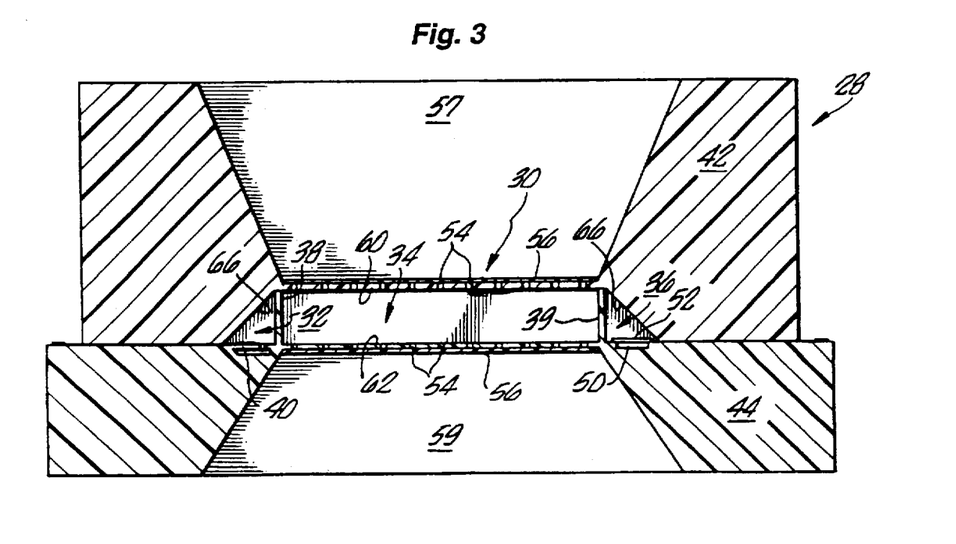
FIG. 3 is a longitudinal cross sectional view along the line 3—3 in FIG. 1.

A first embodiment of the present invention is described in connection with FIGS. 1–3. As shown in FIGS. 1–3, the NDIR gas sensor 28 according to the present embodiment includes an optical waveguide 30. Optical waveguide 30 is comprised of a source chamber 32, sample chamber 34 and detector chamber 36. Source chamber 32 and detector chamber 36 are preferably isolated from the sample chamber 34 by windows 38 and 39, which are interposed in the optical path between the source and detector.

Top substrate 42 and bottom substrate 44 are micromachined from a semiconductor material using well known techniques so that when top substrate 42 is attached to bottom substrate 44 optical waveguide 30 is formed. Preferably substrates 42 and 44 are attached using a standard die-attaching process.

Any semiconductor material may be used for substrates 42 and 44, including Si and GaAs. Si is the preferred semiconductor material.

Other semiconductor materials that may be used for the substrates of the present invention include binary, ternary, and quaternary II-VI and III-V semiconductor materials. In addition, substrates consisting of epitaxially grown germanium on silicon may be used.

Top substrate 42 and bottom substrate 44 may be made out of different semiconductor materials.

Windows 38 and 39, which have been micromachined in bottom substrate 44, divide optical waveguide 30 into source chamber 32, sample chamber 34, and detector chamber 36. Windows 38 and 39 thermally isolate the source and the detector from the gas sample being analyzed so that the gas sample does not cool the detector or source, which would result in an erroneous reading, or at a minimum, reduced sensitivity. The thickness of the windows is selected so as to achieve thermal isolation while at the same time permitting the windows to be optically transparent as to at least desired wavelengths. That is, the thickness of the windows is selected to transmit at least a portion of the light having a desired wavelength, the desired wavelength being dictated by the gas whose concentration is to be measured. As a result, windows 38 and 39 will typically have a thickness in the range of approximately 0.1 mm to 1 mm.

Source chamber 32 contains a radiation source 40. In the present embodiment, source 40 is a black body; thus, source 40 produces radiation of all wavelengths. Radiation from source chamber 32 passes through window 38 into sample chamber 34. Sample chamber 34 contains the gas sample to be analyzed for the concentration of a particular gaseous component. Radiation entering sample chamber 34 passes through the gas sample, and thereafter, the radiation enters detector chamber 36 through window 39 and falls on detector 50 after passing through bandpass filter 52.

Figure 4:
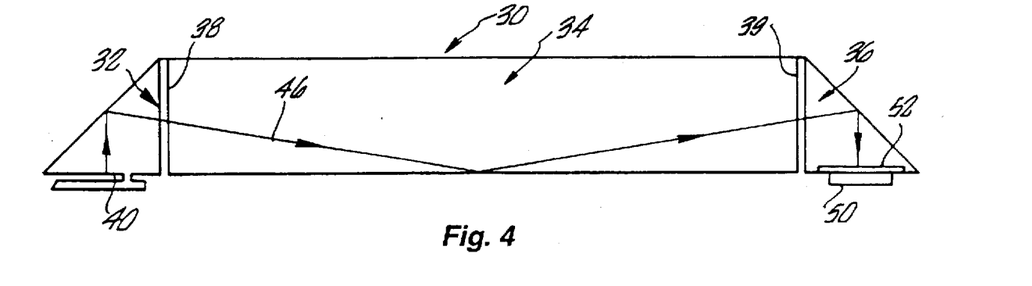
FIG. 4 is simplified optical diagram showing the path of a ray of radiation through the gas sample chamber.

FIG. 4 is a simplified optical diagram showing the optical path taken by a ray 46 emitted by the source 40. As illustrated, ray 46 is reflected multiple times as it progresses down the length of optical waveguide 30 and eventually falls on the detector 50.

Referring back to FIGS. 1-3, bandpass filter 52 is preferably a narrow bandpass interference filter. The purpose of bandpass filter 52 is to remove extraneous wavelengths of radiation from the light produced by black body source 40 so that the detector 50 primarily receives radiation of a wavelength that is strongly absorbed by the gas whose concentration is to be determined.

In the present embodiment, bandpass filter 52 is a thin film interference filter deposited on top of detector 50 and is, therefore, interposed in the optical path between source 40 and detector 50. The method of producing such filters is well known in the art. The theory and physics of interference bandpass filters is described in detail in *The Infrared Handbook* §§ 7.7–7.14 (W. Wolfe & G. Zissis Rev. ed. 3rd printing 1989), hereby incorporated by reference.

The specific characteristics of the bandpass filter simply depends on the wavelength of the radiation absorbed by the gas being analyzed. For example, a bandpass filter that has a center wavelength (CWL) of about 4.26 μm and a full width at half maximum (FWHM) of about 0.1 μm is appropriate for $CO_2$.

Figure 5:
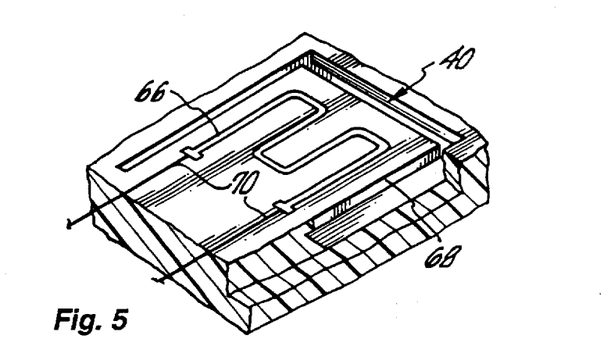
FIG. 5 illustrates a black body light source for use in an NDIR gas sensor according to the present invention.

As noted above, radiation source 40 in the present embodiment is a black body. FIG. 5 illustrates one possible configuration of a black body light source. Black body source 40 is comprised of a thin film resistive heating element 67 deposited on cantilever 68. Thin film resistor 67 may be made out of platinum or other suitable metal. Cantilever 68 is produced using well known micromachining techniques. Such techniques are discussed in K. Petersen, *Silicon as a Mechanical Material*, Proceedings of the IEEE, Vol. 70, No. 5, May 1982, pp. 420–457, hereby incorporated by reference.

Heating element 67 is placed on cantilever 68 to thermally isolate it from substrate 44. Thermal isolation of heating element 67 is important so that the response time of black body source 40 is kept small and so that the entire substrate is not heated. In addition, cantilever 68 prevents heat produced by heating element 67 from draining to substrate 44 too quickly.

Detector 50 may be any device that creates varying electrical responses to corresponding variations in the strength of radiation reaching it from the source. Any of the following detectors may be used when measuring infrared radiation: thermopile, thermocouple, Platinum Silicide Schottky photodiode, and bolometer. A Thermopile is an especially preferred detector for the detection of infrared radiation.

The more recent micromachined electron-tunneling infrared detector disclosed in U.S. Pat. No. 5,265,470, issued Nov. 30, 1993, hereby incorporated by reference, can also be used in the present embodiment to detect infrared radiation.

Sample chamber 34 is a diffusion-type gas sample chamber. Thus, the gas sample contained within sample chamber 34 is present by diffusion only, no pumps are required to push or pull the gas sample into sample chamber 34. To permit gas to diffuse into and out of sample chamber 34, sample chamber 34 contains at least one filtering aperture, of which filtering aperture 54 is typical. The filtering apertures can have a wide variety of shapes and sizes. However, it is preferable to prevent particles of dust and smoke from entering sample chamber 34. To that end, filtering apertures 54 are covered in the present embodiment with a gas permeable layer 56, which serves as a filter. Gas permeable layer 56 preferably keeps out particles of a size greater than about 0.1 μm.

Gas permeable layer 56 may be a dielectric layer that can be deposited by evaporation or sputtering. Silicon oxide, silicon nitride, TEFLON®, and KAPTON® are dielectrics suitable for this purpose, preferably the dielectric layer is silicon oxide or silicon nitride. TEFLON® is the registered trademark for tetrafluoroethylene (TFE) fluorocarbon polymers, and KAPTON® is the registered trademark for polyimide film.

To achieve high rates of diffusion for particles of size less than 0.1 μm, gas permeable layer 56 should be kept quite thin, typically several thousand angstroms. Thus, it is better to have a large number of smaller apertures than a few larger ones.

In the present embodiment, both the top and bottom substrates contain apertures 54 permitting gas to diffuse into and out of the sample chamber. By having apertures 54 in both the top substrate 42 and bottom substrate 44, the gas sample flows more easily into and out of sample chamber 34, especially if the sensor 28 is placed in a flowing gas stream. Of course, however, the apertures may be contained in only the top substrate 42 or bottom substrate 44.

Throat 57 in the top substrate 42 and throat 59 in the bottom substrate 44 merely permit substrates 42 and 44 to have thicker cross sections while at the same time reducing the amount of semiconductor material that must be etched through to form apertures 54 in walls 60 and 62 of optical waveguide 30. This enhances the overall structural integrity of sensor 28 without increasing the difficulty of etching apertures 54 in the substrates. Throats 57 and 59, however, are not required. Thinner blocks of semiconductor material can be used to produce substrates 42 and 44 without increasing the difficulty of etching holes in walls 60 and 62 of the waveguide to form apertures 54.

For ease of manufacture, it is preferred that the sample chamber 34 have a square or rectangular cross section. But, other shapes can also be used. For example, sample chamber 34 in waveguide 30 can have a circular or triangular shape. Source chamber 32 and detector chamber 36 are similarly not limited to the preferred embodiment shapes.

If silicon is used as the semiconductor material for substrates 42 and 44, only about half of the light will be reflected from the walls of the optical waveguide because silicon is only about 50% reflective. The efficiency of an NDIR detector according to the present embodiment may be improved, therefore, by metallizing at least a portion of the inwardly facing walls of optical waveguide 30. Of course windows 38 and 39 should not be metallized in such a manner as to prevent detector 50 from receiving the wavelength of light that is strongly absorbed by the gas whose concentration is being measured. This would naturally defeat the purpose of the waveguide. Thus, in the present embodiment, only the side walls 58, upper wall 60 and lower wall 62 of the sample chamber are metallized. And in the source and detector chambers, only side walls 64 and upper walls 66 are metallized.

A variety of different metallizations can be used to increase the reflectivity of the inwardly facing walls of optical waveguide 30, including Al, Au, Cr, Ni, and Pt. Each of these metals are easily deposited on the surface of the inwardly facing walls of waveguide 30 using vapor deposition techniques well known in the art.

To ensure that the full benefit of the metallization is achieved, the metallization must be thicker than the skin depth for the particular metal selected at the wavelength being used to measure the concentration of the desired gas. If the metallization is not sufficiently thick, the electric field will penetrate the metallization and interact with the Si substrate; thus reducing the amount of light reflected.

In the present and subsequent embodiments, Applicant has described the use of a top substrate 42 and a bottom substrate 44 to form gas sensor 28. However, to the extent that gas sensor 28 is micromachined from a single substrate, the resulting gas sensor would still fall within the scope of the present invention.

Figure 6:
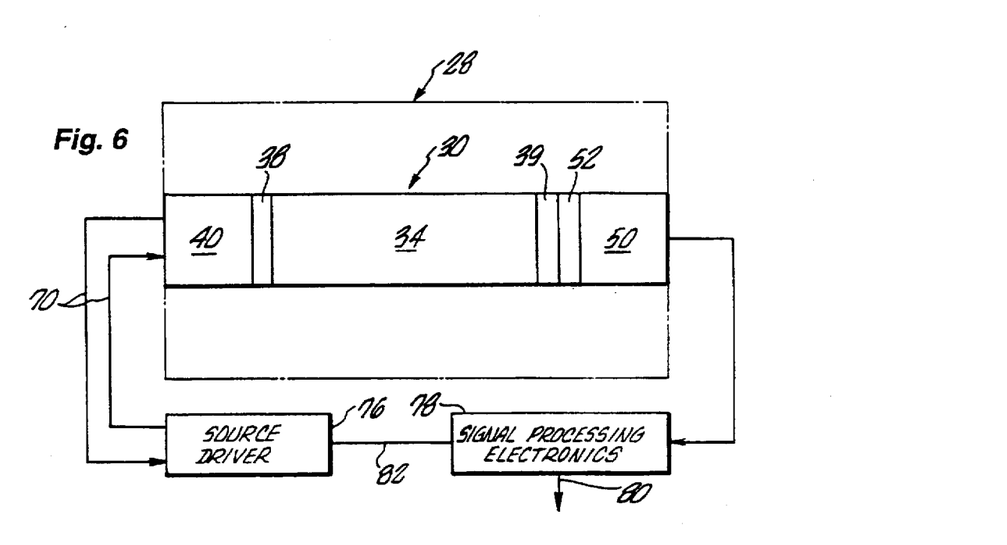
FIG. 6 is a schematic diagram of a system using a gas sensor according to the present invention.

The NDIR gas sensor 28 can be used in a system such as the one illustrated schematically in FIG. 6. The broken line 28 represents the NDIR gas sensor 28 shown in more detail in FIGS. 1–3.

In operation, source 40 is energized through an electric current delivered by source driver 76 through a circuit including leads 70. As is well known in the art, source driver 76 delivers power to source 40 in pulses at a set frequency to modulate the source so that synchronous detection can be achieved. Typically, source driver 76 delivers pulses of energy at a frequency of 1 Hz, 2 Hz, or 3 Hz.

After the radiation from source 40 reaches detector 50, detector 50 produces an electrical signal that represents the intensity of the radiation falling on it. This signal is inversely proportional to the amount of gas being detected. For example, if $CO_2$ is being detected, the more $CO_2$ there is in sample chamber 34 the weaker the infrared spectrum will be striking detector 50. The electrical signal produced by detector 50 is applied to an electronic circuit 78 that converts it to a signal which represents the concentration of the gas in question. The signal output 80 of the signal processing electronics 78 may be applied to a meter, an alarm, process control means or the like as is well known in the art.

The source driver 76 and signal processing electronics 78 are in electronic communication through line 82 so that the entire system is coordinated and synchronous detection can be achieved. The signal processing is generally straight forward and is taught in a number of places, including, for example, U.S. Pat. No. 4,578,762, hereby incorporated by reference, and U.S. Pat. No. 4,694,173, hereby incorporated by reference.

In practice, a device embodying the present invention may be calibrated by placing it within a bell jar and purging the bell jar with nitrogen. When the bell jar has been thoroughly purged with nitrogen, the zero condition for the sensor is established. Thereafter, a gas whose concentration will be measured by the sensor is fed into the bell jar in a gas stream of known concentration. For example, if $CO_2$ is the desired gas then the bell jar would be purged with a gas having a $CO_2$ concentration of 5% until the concentration of the gas within the bell jar stabilizes. The signal processing electronics 78 are then manipulated until a reading of 5% is obtained from the sensor 28. This process is repeated using gases having different concentrations of $CO_2$ until the NDIR gas sensor 28 is calibrated over the desired range of concentrations.

In the present embodiment, source 40 and detector 50 are both fabricated on the same substrate. However, as would be apparent to a person of ordinary skill in the art, source 40 and detector 50 could be fabricated on different substrates. But, by fabricating both source 40 and detector 50 on the same substrate 44, the fabrication of the NDIR gas sensor 28 is simplified.

Figure 7:
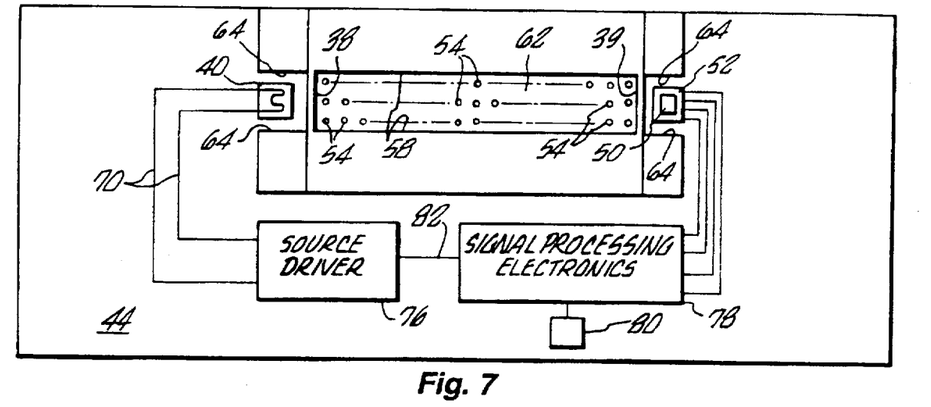
FIG. 7 is a plan view of a bottom substrate for fabricating a gas sensor according to a second embodiment.

A plan view of a bottom substrate 44 according to a second embodiment of the present invention is illustrated in FIG. 7. As shown in FIG. 7, if source 40 and detector 50 are both fabricated on substrate 44, the source driver 76 and signal processing electronics 78 may also be fabricated on substrate 44 near the source and detector using standard IC fabrication techniques. Substrate 44 is identical to substrate 44 of the first embodiment, which is illustrated in FIGS. 1–3, in all other respects.

Top substrate 42 is not shown. However, it is identical to the top substrate 42 shown in FIGS. 1–3.

By virtue of free diffusion of gas through layer 56 that covers the filtering apertures 54, the gas sample chamber 34 is always filled with gas. As a result, there is a possibility that if the ambient temperature falls sufficiently, water vapor or one of the other gases in the sample chamber will condense to a liquid state and be deposited in the form of small droplets on the interior walls of gas sample chamber 34. This would interfere with the internal reflectivity that is needed for operation of waveguide 30, and would lead to erroneous results.

Figure 8:
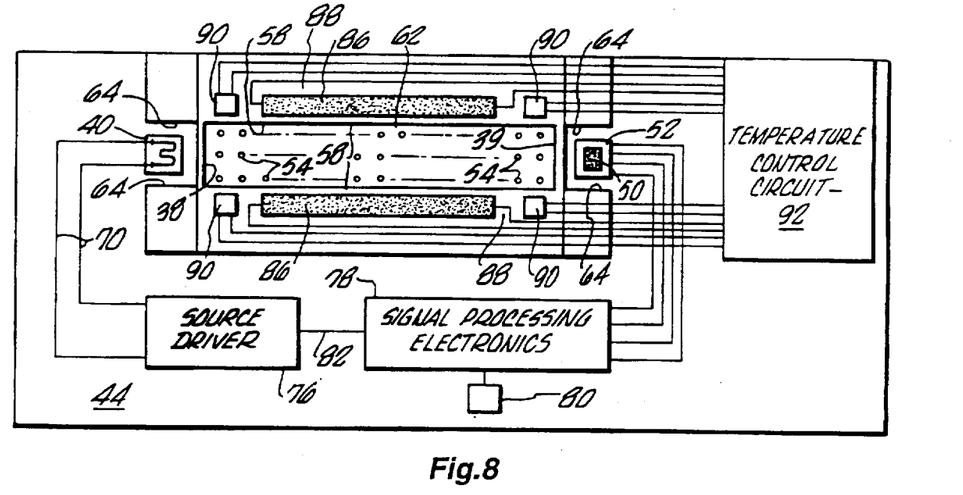
FIG. 8 is a plan view of a bottom substrate for fabricating a gas sensor according to a third embodiment.

To prevent this from happening, and thus increase the efficiency and repeatability of the transmission of radiation, a particularly preferred bottom substrate 44 as shown in FIG. 8 may be used to fabricate an NDIR gas sensor 28 according to a third embodiment. As in the previous embodiment, top substrate 42 is not shown. Again, however, it is identical to the top substrate 42 illustrated in FIGS. 1–3 so that when it is attached to substrate 44, NDIR gas sensor 28 is formed.

As shown in FIG. 8, a thin film resistive type heater 86 is added to the top of each boss 88. Bosses 88 have been micromachined into substrate 44 and form the sidewalls of optical waveguide 30. Thin film resistance temperature detectors (RTD's) 90 measure the temperature of sidewalls 58 of the sample chamber 34. The heaters 86 and the thin film RTD's 90 are connected to a temperature control circuit 92, which functions as a closed loop controller that operates in a well-known way to maintain the sample chamber at a set temperature.

As with the source driver 76 and signal processing electronics 78, the temperature control circuit 92 may be fabricated on substrate 44 using standard IC fabrication techniques.

Because the gas sensor of the present invention is fabricated from a semiconductor material such as silicon, other semiconductor integrated circuit devices may also be added wherever needed to further enhance the performance of the NDIR gas sensor 28 according to the present invention. For example, temperature sensors, pressure transducers, and humidity sensors may be added to accomplish any of the signal compensation schemes known in the art. In addition, a micro-flow sensor may be added to detect the flow rate of the sample gas through the sample chamber.

Figure 10:
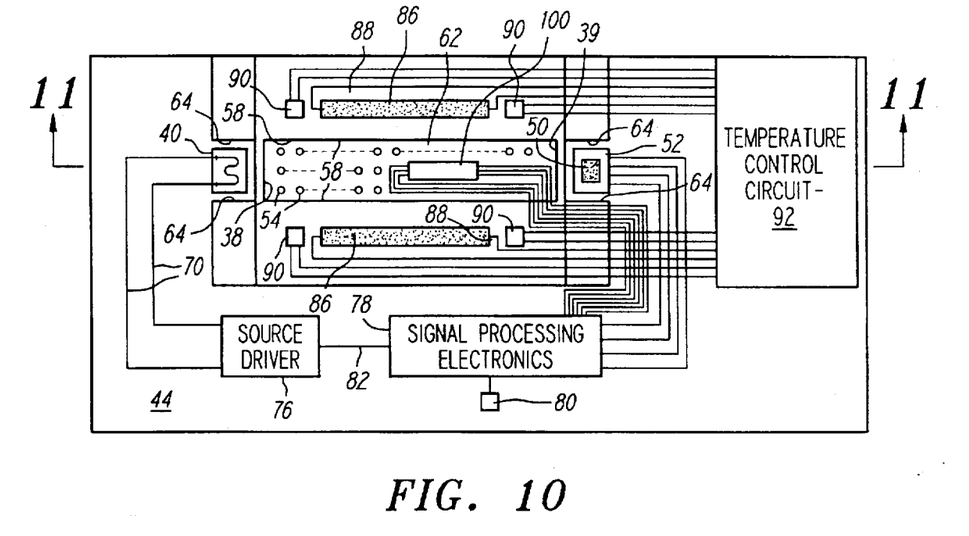
FIG. 10 is a plan view of a bottom substrate for fabricating a gas sensor according to the third embodiment with additional performance enhancing semiconductor devices fabricated thereon.
Figure 11:
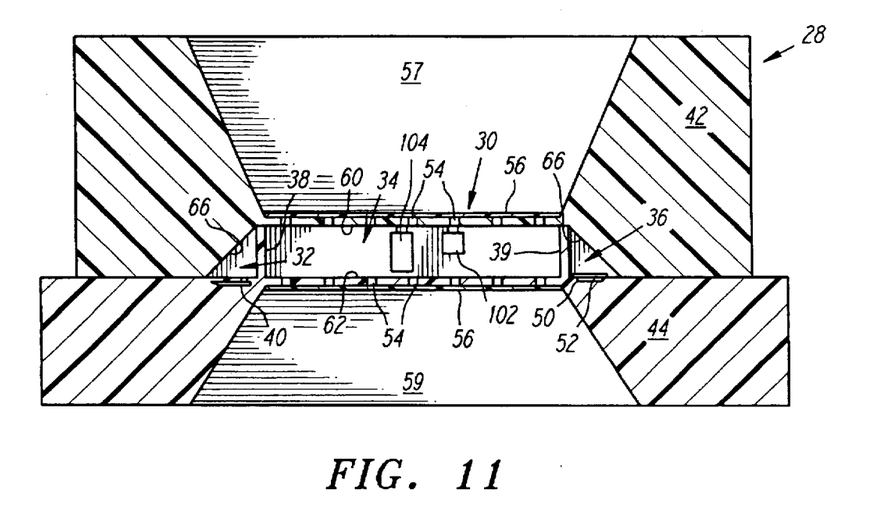
FIG. 11 is a longitudinal cross sectional view along line 11—11 in FIG. 10, except that the cross section is taken through a complete NDIR gas sensor according to the present invention rather than just the bottom substrate.

FIG. 10 shows a plan view of a bottom substrate 44 according to the embodiment illustrated in FIG. 8 with the addition of further performance enhancing semiconductor devices manufactured thereon. Namely, a humidity sensor 100 has been added to the bottom substrate 44 to monitor the humidity level in the sample chamber 32 during operation of the NDIR gas sensor. In the present embodiment, humidity sensor 100 is a thin film capacitive humidity sensor. As illustrated in FIG. 11, bottom substrate 44 also has manufactured thereon, using techniques well known in the art, a pressure transducer 102 and a flow meter 104. The output from these devices is communicated to the signal processing electronics 78 to incorporate into the signal compensation schemes known in the art.

A fourth embodiment of the present invention is described in connection with FIG. 9. This embodiment is preferred when the ability to detect multiple gases is desired or when a reference detector is desired.

According to this embodiment, a bottom substrate 44 is provided. Bottom substrate 44 can have the basic features of any of the previous embodiments. However, instead of a single detector 50 and bandpass filter 52 being fabricated on substrate 44, a plurality of detectors 50 and bandpass filters 52 are fabricated on substrate 44 so that when top substrate 42, which has been omitted from FIG. 9, is attached they are all within the detector chamber 36.

Each bandpass filter 52 is interposed in the optical path between the light source 40 and one of the plurality of detectors 50. The number of gases whose concentration is desired to be determined dictates the specific number of detectors 50 and bandpass filters 52 that are required.

Each bandpass filter 52 is designed so that the detector 50 it is associated with primarily receives radiation of a wavelength that is strongly absorbed by the gas whose concentration that specific detector 50 is to determine. Thus, the illustrated substrate 44 can be used to form an NDIR gas sensor that can simultaneously determine the concentration of a plurality of gases.

Of course, the source driver 76 and signal processing electronics 78 may be added to substrate 44 in this embodiment. Similarly, if desired, the heaters 86, RTD's 90 and temperature control circuit 92 shown in FIG. 8 may also be added to substrate 44.

Figure 9:
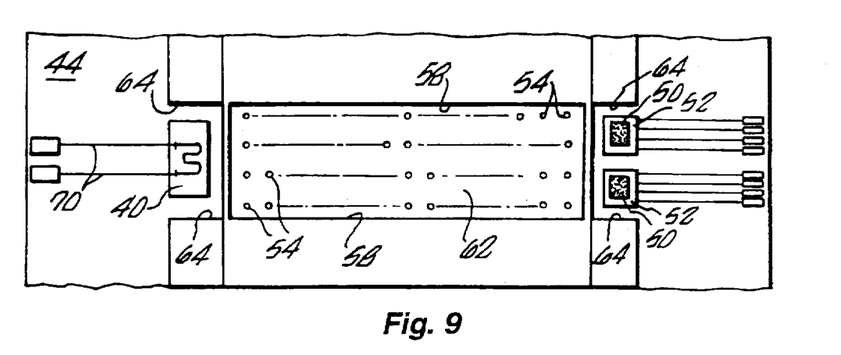
FIG. 9 is a plan view of a bottom substrate for fabricating a gas sensor according to a forth embodiment.

Alternatively, if desired, in this embodiment one of the detectors 50 shown on substrate 44 in FIG. 9 may be used as a reference detector. The reference detector provides the signal processing electronics 78 with a baseline output signal against which to compare the output signal from the detector that is being used to measure the concentration of the desired gas. As a result, the intrinsic stability of the sensor over time may be improved because variations in the light intensity from source 40 are compensated for.

If one of the detectors 50 is to be used as a reference detector, the bandpass filter 52 associated with it must be designed so that the detector primarily receives radiation of a neutral wavelength. In other words, the bandpass filter 52 must primarily pass radiation that is not absorbed by the gas sample within sample chamber 34 and filter out other extraneous wavelengths of radiation.

If there are more than two detectors within sample chamber 36, more than one of them may be used as a reference detector. For example, if there are three detectors 50 within detector chamber 36, two of them could be used as reference detectors, the bandpass filter 52 for each passing a different neutral wavelength. The third detector in this situation would be used to determine the concentration of a desired gas.

Therefore, as would be apparent to one of ordinary skill in the art, the NDIR gas sensor 28 according to the present embodiment is very flexible. It may be used to measure the concentration of a plurality of different gases, or it may be used to measure the concentration of one or more gases while simultaneously using at least one reference detector to maintain the intrinsic stability of the sensor over time.

An NDIR gas sensor 108 according to a fifth embodiment is now described in connection with FIGS. 12–15. As the present embodiment has many of the same features discussed in the previous embodiments, like reference numbers have been used to refer to like features.

In the present embodiment, rather than locating radiation source 40 and detector 50 at opposing ends of the sample chamber 34, the radiation source 40 and detector 50 are provided at the same end of the sample chamber 34 in a side by side relationship. An advantage of this relationship as opposed to an NDIR gas sensor which has a straight optical waveguide with a light source and a light detector provided at opposing ends is that the NDIR gas sensor 108 of the present embodiment is twice as sensitive. Thus, the NDIR gas sensor of the present embodiment can achieve the same sensitivity with a sample chamber half as long.

Figure 12:
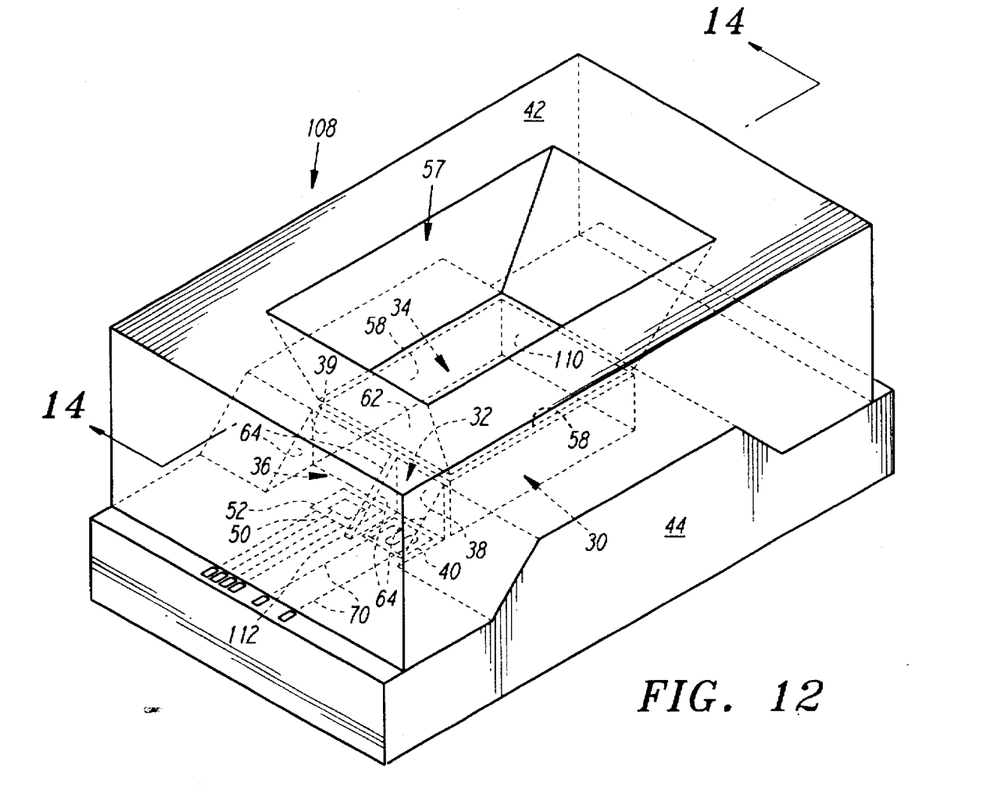
FIG. 12 is an oblique view of an NDIR gas sensor according to a fifth embodiment.
Figure 13:
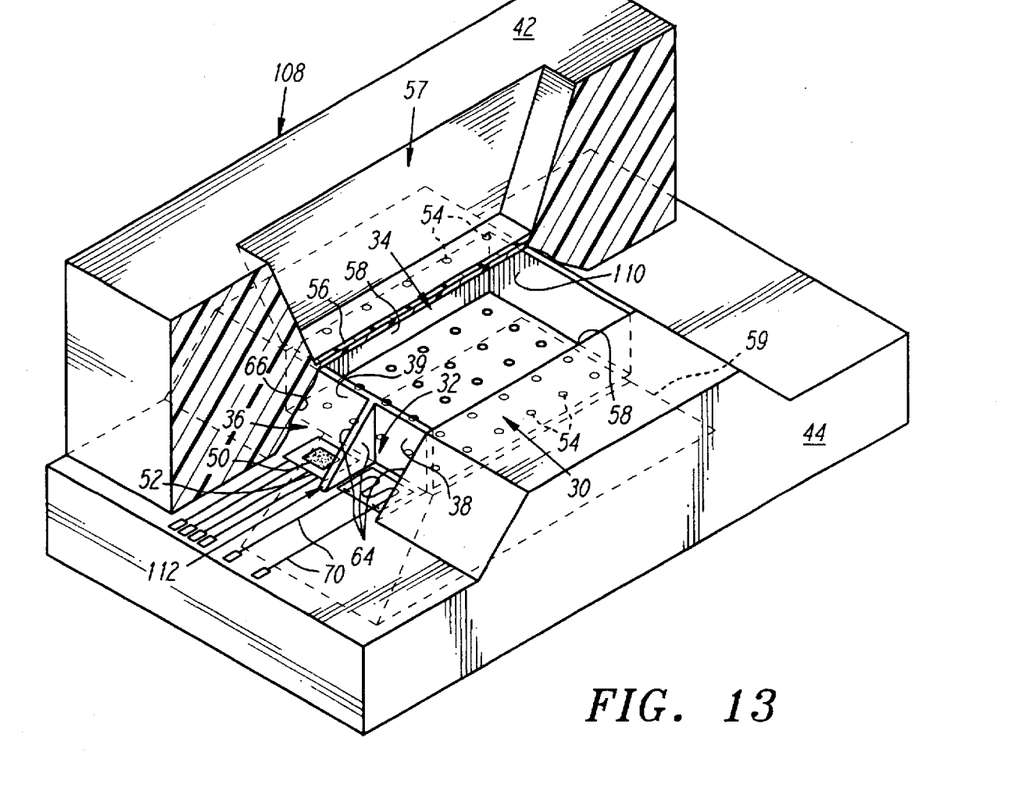
FIG. 13 is an oblique view showing a partial cutaway of an NDIR gas sensor according to the fifth embodiment.
Figure 14:
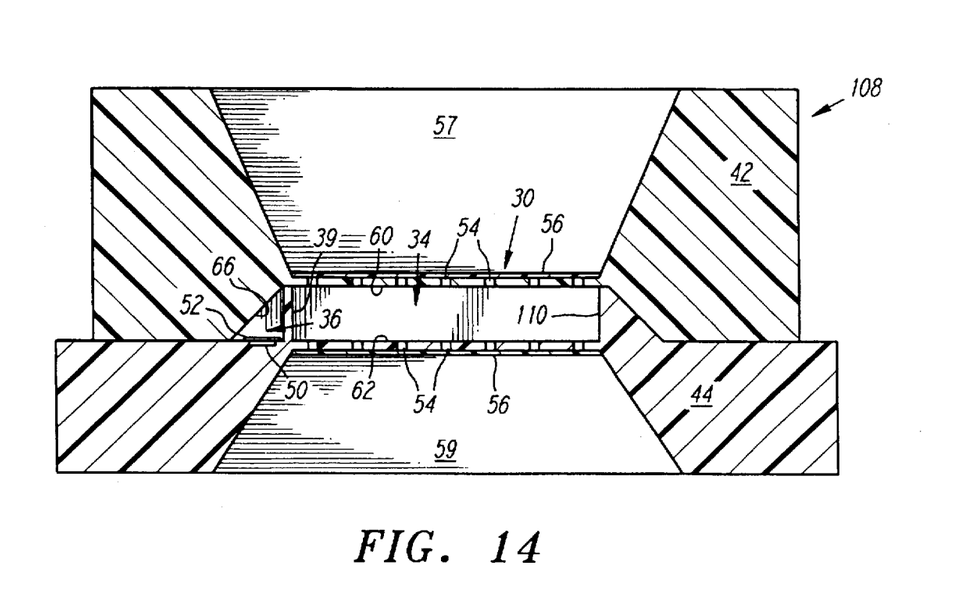
FIG. 14 is a longitudinal cross sectional view along line 14—14 in FIG. 12.

As shown in FIGS. 12–14, NDIR gas sensor 108 according to the present embodiment includes an optical waveguide 30. Optical waveguide 30 is comprised of source chamber 32, sample chamber 34, and detector chamber 36. Source chamber 32 and detector chamber 36 are located on the same end of optical waveguide 30, and sample chamber 34 is disposed in the optical path between the two. Source chamber 32 and detector chamber 36 are preferably isolated from the sample chamber 34 by windows 38 and 39, which are also interposed in the optical path between the source and detector.

Top substrate 42 and bottom substrate 44 are micromachined from a semiconductor material using well known techniques so that when top substrate 42 is attached to bottom substrate 44 optical waveguide 30 is formed. Preferably substrate 42 and 44 are attached using a die-attaching process.

As with the first embodiment, any semiconductor material may be used for substrates 42 and 44, including Si and GaAs. Si, however, is the preferred semiconductor material, and preferably substrates 42 and 44 are made out of the same semiconductor material.

In the present embodiment, sample chamber 34 includes an optically open end defined by windows 38 and 39 and an optically closed end defined by end wall 110. Source 40 and detector 50 preferably occupy off-center positions at the optically open end of sample chamber 34. The end of the sample chamber defined by windows 38, 39 is referred to as being optically open because radiation of relevant wavelengths can pass through windows 38 and 39. The end of the sample chamber 34 defined by end wall 110 is referred to as being optically closed because the majority of radiation striking end wall 110 from source 40 is reflected back toward windows 38, 39.

Windows 38, 39 and divider 112, which have been micromachined in bottom substrate 44, divide optical waveguide 30 into source chamber 32, sample chamber 34, and detector chamber 36. Windows 38 and 39 thermally isolate the source and the detector from the gas sample being analyzed so that the gas sample does not cool the detector or source, which would result in an erroneous reading, or at a minimum, reduced sensitivity. As with the first embodiment, the thickness of the windows should be selected so as to achieve thermal isolation while at the same time permitting the windows to be optically transparent to desired wavelengths.

Divider 112 thermally isolates detector 50 from source 40. Divider 112 should also have sufficient thickness to prevent light from source 40 from entering detector chamber 36. Any such light transmittance would have an obvious deleterious effect on the ability of the gas sensor 108 to accurately measure the concentration of the gas to be detected. To ensure that no light is transmitted through divider 112 and that divider 112 provides good thermal isolation, side walls 64 of divider 112 can be metallized. Indeed, the efficiency of an NDIR gas sensor 108 according to the present embodiment can be improved by metallizing the walls of optical waveguide 30. Of course windows 38 and 39 should not be metallized in such a manner as to prevent detector 50 from receiving the wavelength of light that is strongly absorbed by the gas whose concentration is to be measured. This would naturally defeat the purpose the waveguide. Thus, in the present embodiment, the side walls 58, upper wall 60, lower wall 62 and end wall 110 of the sample chamber are metallized. And in the source and detector chambers, side walls 64 and upper wall 66 are metallized.

A variety of different metallizations can be used to increase the reflectivity of the walls of optical waveguide 30, including Al, Au, Cr, Ni, and Pt. Each of these metals are easily deposited on the surface of the inwardly facing walls of waveguide 30 using vapor deposition techniques well known in the art.

To ensure that the full benefit of the metallization is achieved, the metallization must be thicker than the skin depth for the particular metal selected at the wavelength being used to measure the concentration of the desired gas. If the metallization is not sufficiently thick, the electric field will penetrate the metallization and interact with the Si substrate; thus reducing the amount of light reflected.

Source chamber 32 contains a radiation source 40. In the present embodiment, source 40 is a black body; thus, source 40 produces radiation of all wavelengths. In the simplest mode of propagation, radiation from source chamber 32 passes through window 38 into sample chamber 34, passes through the gas sample, reflects off end wall 110, passes through the gas a second time, and thereafter, the radiation enters detector chamber 36 through window 39 and falls on detector 50 after passing through bandpass filter 52. An important advantage of using the NDIR gas sensor 108 of the present embodiment, however, is that sample chamber 34 permits other modes of propagation from the source to the detector to occur. The amount of radiation contributed by the various modes of transmission is additive since the successive modes are characterized by progressively steeper angles of reflection of the light rays. Further, the radiation travels a greater distance through the space within sample chamber 34 as the order of the mode of propagation increases. That is, for the higher modes, the angle of reflection of the light rays is steeper resulting in a greater distance of travel back and forth across the sample chamber 34, notwithstanding that the distance traveled in the longitudinal direction remains constant and simply equals twice the length of the optical waveguide.

In the present embodiment, bandpass filter 52 is a thin film interference filter deposited on top of detector 50 and is, therefore, interposed in the optical path between source 40 and detector 50.

The specific characteristics of the bandpass filter simply depends on the wavelength of the radiation absorbed by the gas being analyzed. For example, a bandpass filter that has a center wavelength (CWL) of about 4.26 µm and a full width at half maximum (FWHM) of about 0.1 µm is appropriate for $CO_2$.

As noted above, radiation source 40 in the present embodiment is a black body. FIG. 5 illustrates one possible configuration of a black body light source for the present embodiment.

Detector 50 may be any device that creates varying electrical responses to corresponding variations in the strength of radiation reaching it from the source. Any of the following detectors may be used when measuring infrared radiation: thermopile, thermocouple, Platinum Silicide Schottky photodiode, and bolometer. A Thermopile is an especially preferred detector for the detection of infrared radiation.

The more recent micromachined electron-tunneling infrared detector disclosed in U.S. Pat. No. 5,265,470 can also be used in the present embodiment to detect infrared radiation.

Sample chamber 34 is a diffusion-type gas sample chamber. To permit gas to diffuse into and out of sample chamber 34, sample chamber 34 contains at least one filtering aperture, of which filtering aperture 54 is typical. The filtering apertures can have a wide variety of shapes and sizes. However, it is preferable to prevent particles of dust and smoke from entering sample chamber 34. To that end, filtering apertures 54 are covered in the present embodiment with a gas permeable layer 56, which serves as a filter. Gas permeable layer 56 preferably keeps out particles of a size greater than about 0.1 µm.

Gas permeable layer 56 may be a dielectric layer that can be deposited by evaporation or sputtering. Silicon oxide, silicon nitride, TEFLON®, and KAPTON® are dielectrics suitable for this purpose, preferably the dielectric layer is silicon oxide or silicon nitride. TEFLON® is the registered trademark for tetrafluoroethylene (TFE) fluorocarbon polymers, and KAPTON® is the registered trademark for polyimide film.

To achieve high rates of diffusion for particles of size less than 0.1 µm, gas permeable layer 56 should be kept quite thin, typically several thousand angstroms. Thus, it is better to have a large number of smaller apertures than a few larger ones.

In the present embodiment, both the top and bottom substrates contain apertures 54 permitting gas to diffuse into and out of the sample chamber. By having apertures 54 in both the top substrate 42 and bottom substrate 44, the gas sample flows more easily into and out of sample chamber 34, especially if the sensor 108 is placed in a flowing gas stream. Of course, however, the apertures may be contained in only the top substrate 42 or bottom substrate 44.

Throat 57 in the top substrate 42 and throat 59 in the bottom substrate 44 merely permit substrates 42 and 44 to have thicker cross sections while at the same time reducing the amount of semiconductor material that must be etched through to form apertures 54 in walls 60 and 62 of optical waveguide 30. This enhances the overall structural integrity of sensor 108 without increasing the difficulty of etching apertures 54 in the substrates. Throats 57 and 59, however, are not required. Thinner blocks of semiconductor material can be used to produce substrates 42 and 44 without increasing the difficulty of etching holes in walls 60 and 62 of the waveguide to form apertures 54.

For ease of manufacture, it is preferred that the sample chamber 34 have a rectangular cross section in the present embodiment. But, other shapes can also be used. For example, sample chamber 34 in waveguide 30 can have a circular or triangular shape. Source chamber 32 and detector chamber 36 are similarly not limited to the preferred embodiment shapes.

The operation and calibration of NDIR gas sensor 108 according to the present embodiment is the same as that described in connection with the NDIR gas sensor 28 described in connection with FIGS. 1–6.

In the present embodiment, source 40 and detector 50 are both fabricated on the same substrate. However, as would be apparent to a person of ordinary skill in the art, source 40 and detector 50 could be fabricated on different substrates. But, by fabricating both source 40 and detector 50 on the same substrate 44, the fabrication of the NDIR gas sensor 108 is simplified.

Figure 15:
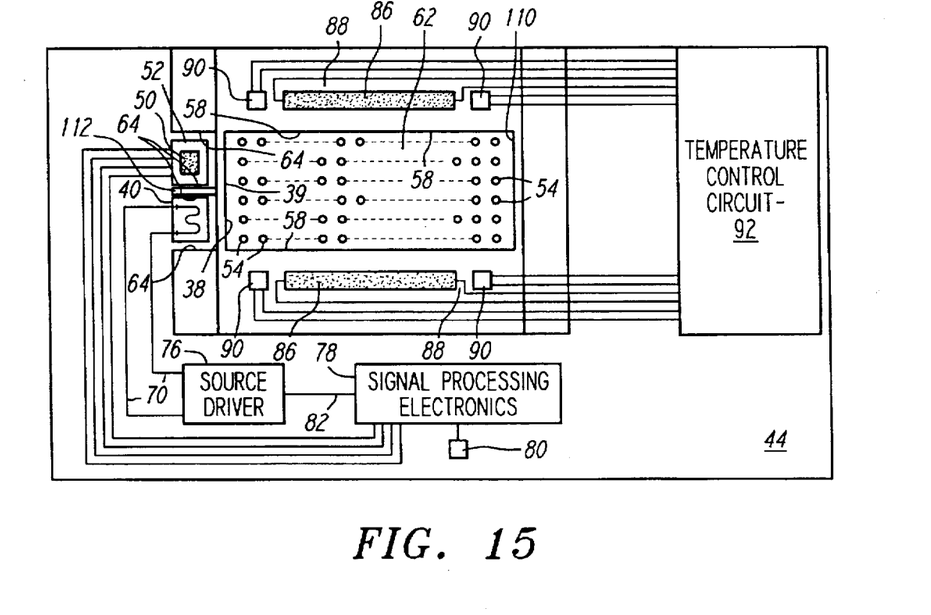
FIG. 15 is plan view of a bottom substrate for fabricating an NDIR gas sensor according to the fifth embodiment.

As illustrated in connection with FIG. 15, source driver 76 and signal processing electronics 78 may also be fabricated on substrate 44 near the source and detector using standard IC fabrication techniques. The performance of the NDIR gas sensor 108 according to the present embodiment can also be improved by adding a thin film resistive type heater 86 and thin film RTD's 90 to the top of each boss 88 to prevent moisture from condensing on the interior walls of sample chamber 34. Operation of these devices was previously described in connection with FIG. 8.

Other semiconductor integrated circuit devices may also be added wherever needed to further enhance the performance of the NDIR gas sensor 108 according to the present invention. For example, temperature sensors, pressure transducers, and humidity sensors may be added to accomplish any of the signal processing schemes known in the art.

Figure 16:
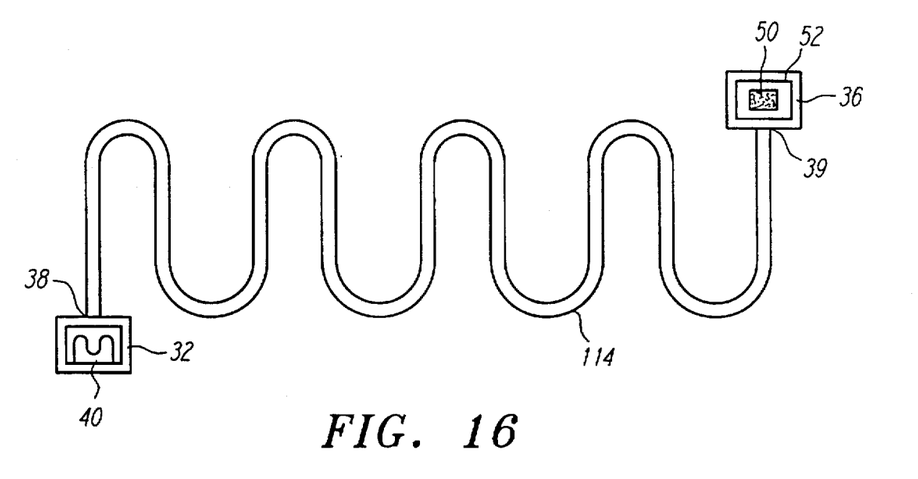
FIG. 16 is a schematic diagram of one possible extended sample chamber for an NDIR gas sensor according to a sixth embodiment.
Figure 17:
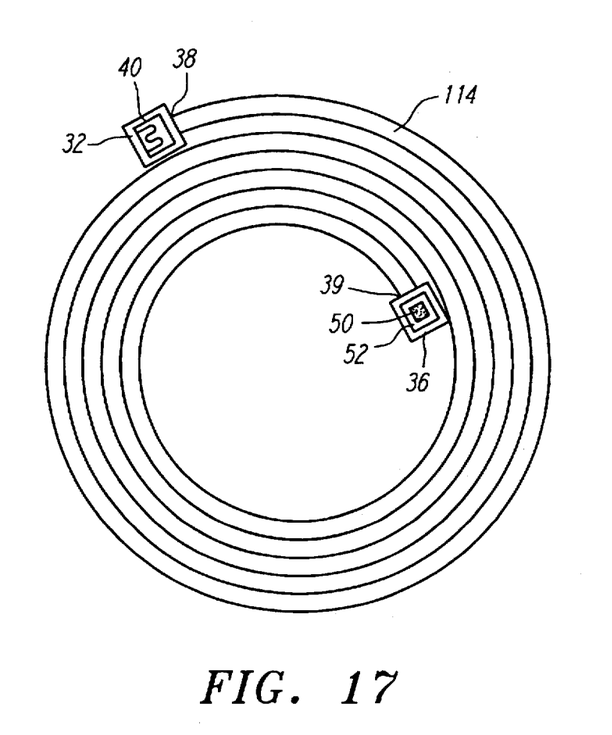
FIG. 17 is a schematic diagram of a second possible extended sample chamber for an NDIR gas sensor according to the sixth embodiment.

A sixth embodiment of the present invention is now described in connection with FIGS. 16 and 17.

Certain gases have absorption bands that absorb so weakly that absorption can only be detected after the radiation has traveled a relatively long distance, perhaps tens of meters, through the sample gas. In other situations, the gases of interest might have adequate absorption strengths but they must be detected in very low concentrations, typically in parts per million (ppm) or less, so that long path lengths are required in this situation also.

In the various embodiments of the invention described in connection with FIGS. 1 through 11, a straight sample chamber 34 was employed. By using a straight sample chamber 34, however, the length of the optical waveguide 30, and thus the sensitivity of the NDIR gas sensor 28, is physically limited by the length of the substrate 44. As a result, the NDIR gas sensors described in connection with those figures may have insufficient path lengths to adequately monitor the concentration of certain gases. In the present embodiment, as illustrated schematically in FIGS. 16 and 17, an optical waveguide is employed that includes an extended sample chamber 114 that extends along an indirect path. Preferably the indirect path traversed by the extended sample chamber 114 according to the present embodiment has a serpentine shape as illustrated in FIG. 16 or a spiral shape as illustrated in FIG. 17. The remaining features and possible modifications of the NDIR gas sensor 28 according to the present embodiment are identical to those described in connection with the embodiments illustrated in FIGS. 1–11. Thus, as with the embodiments described in connection with FIGS. 1–11, the light source 40 and light detector 50 of the present NDIR gas sensor are located at opposite ends of the optical waveguide 30, and a pair of windows 38, 39 are preferably disposed between the light source and detector so as to define a sample chamber therebetween.

An advantage of the present embodiment is that a sample chamber having a path length much longer than the length of the substrate in which it is formed can be produced, thus providing enhanced sensitivity to the NDIR gas sensor without substantially increasing its overall dimensions.

The walls of the extended sample chamber 114 preferably have a mirror like finish. This can be accomplished by metallizing the walls of the sample chamber with a metal such as Al, Au, Cr, Ni, or Pt. As a result of its specularly reflective surface, the radiation that has been directed into the extended sample chamber 114 will progress by successive reflections through the sample chamber, and a fraction of the radiation will reach the other end of the sample chamber 114, enter detector chamber 36 through window 39, and eventually fall on detector 50 after passing through bandpass filter 52.

A number of apertures, such as filtering apertures 54 shown in FIGS. 2, and 7–9, permit communication between the extended sample chamber 114 and the air in the space surrounding the gas sample chamber. The gas whose concentration is to be measured freely enters and exits the extended sample chamber 114 by diffusion through these passages.

The longer the extended sample chamber 114 is, the less radiation that will reach the detector end of the optical waveguide 30. As a result, there is a trade-off between the diminishing intensity that results as the path length is made longer against the increased absorption that is available with a longer path length. Thus, when determining the appropriate path length for the sample chamber 114 for an NDIR gas sensor according to the present embodiment, the following factors should be taken into account: (1) the particular gas to be detected, (2) the intensity of the source 40, and (3) the sensitivity of the detector 50.

Operation and calibration of an NDIR gas sensor 28 employing an extended sample gas chamber 114 is much the same as that described in connection with the embodiment illustrated in FIGS. 1–11.

While the present invention has been made clear in the illustrative embodiments, it will be immediately obvious to those skilled in the art that many modifications of structure, arrangement, proportions, the elements, materials, and components used in the practice of the invention, and otherwise, which are particularly adapted to specific environments and operative requirements, can be made without departing from the principles disclosed. Thus, it is to be clearly understood that this description is made only by way of example and not as a limitation to the scope of the invention as claimed below.

I claim:

1. An improved NDIR gas sensor, comprising:
   a. a first semiconductor material substrate;
   b. a second semiconductor material substrate attached to the first substrate;
   c. an optical waveguide formed between the first and second substrates;
   d. a light source integrally formed on one of the substrates and positioned at one end of the optical waveguide;
   e. a light detector integrally formed on one of the substrates and positioned at the end of the optical waveguide opposite the light source;
   f. a bandpass filter interposed in the optical path between the light source and light detector;
   g. a pair of windows interposed in the optical path between the light source and light detector so as to define therebetween a sample chamber within the waveguide and thermally isolate the light source and light detector, the pair of windows being micromachined from one of the semiconductor material substrates, and wherein the sample chamber extends along an indirect path; and
   h. means for permitting diffusion of gas into and out of the sample chamber.

2. An NDIR gas sensor according to claim 1, wherein the light source and light detector are fabricated on the same substrate.

3. An NDIR gas sensor according to claim 1, wherein at least a portion of the walls of the optical waveguide are metallized to improve internal reflectivity of the waveguide.

4. An NDIR gas sensor according to claim 1, further comprising means for heating the walls of the optical waveguide to a temperature above the dew point of the gas in the sample chamber.

5. An NDIR gas sensor according to claim 1, wherein the light detector is an infrared detector selected from the group consisting of Platinum Silicide Schottky photodiode, bolometer, infrared tunnel sensor, thermocouple, and thermopile.

6. An NDIR gas sensor according to claim 1, further comprising:
   a. a source driver for energizing the source at a preset frequency; and
   b. signal processing electronics for converting the electrical output produced by the detector into a signal which represents the concentration of the gas being measured.

7. An NDIR gas sensor according to claim 1, wherein the means for permitting gas to diffuse into and out of the space within the sample chamber comprises at least one aperture in a wall of the sample chamber.

8. An NDIR gas sensor according to claim 1, wherein the means for permitting gas to diffuse into and out of the sample chamber comprises:
   a. a plurality of apertures in at least one wall of the sample chamber; and
   b. a gas permeable layer covering the plurality of apertures.

9. An NDIR gas sensor according to claim 8, wherein the gas permeable layer is made from a dielectric selected from the group consisting of TFE fluorocarbon polymers, polyimide, silicon oxide, and silicon nitride.

10. An NDIR gas sensor according to claim 8, wherein the gas permeable layer prevents particles larger than 0.1 μm from entering the sample chamber within the optical waveguide.

11. An NDIR gas sensor according to claim 1, further comprising:
    a. a plurality of light detectors integrally formed on one of the substrates and positioned at the end of the optical waveguide opposite the light source;
    b. a plurality of bandpass filters, wherein each bandpass filter passes a different range of wavelengths and is interposed between the light source and one of the plurality of light detectors.

12. An NDIR gas sensor according to claim 11, wherein at least one of the plurality of bandpass filters is designed to pass a neutral wavelength.

13. An improved NDIR gas sensor, comprising:
    a. a first semiconductor material substrate;
    b. a second semiconductor material substrate attached to the first substrate;
    c. an optical waveguide formed between the first and second substrates;
    d. a light source integrally formed on one of the substrates and positioned at one end of the optical waveguide;
    e. a light detector integrally formed on one of the substrates and positioned at the end of the optical waveguide opposite the light source;
    f. a bandpass filter interposed in the optical oath between the light source and light detector;
    g. a pair of windows interposed in the optical path between the light source and light detector so as to define therebetween a sample chamber within the waveguide and thermally isolate the light source and light detector, wherein the sample chamber extends along an indirect path;
    h. means for permitting diffusion of gas into and out of the sample chamber; and
    i. means for sensing the humidity level in the optical waveguide sample chamber.

14. An improved NDIR gas sensor, comprising:
    a. a first semiconductor material substrate;
    b. a second semiconductor material substrate attached to the first substrate;
    c. an optical waveguide formed between the first and second substrates;
    d. a light source integrally formed on one of the substrates and positioned at one end of the optical waveguide;
    e. a light detector integrally formed on one of the substrates and positioned at the end of the optical waveguide opposite the light source;
    f. a bandpass filter interposed in the optical path between the light source and light detector;
    g. a pair of windows interposed in the optical path between the light source and light detector so as to define therebetween a sample chamber within the waveguide and thermally isolate the light source and light detector, wherein the sample chamber extends along an indirect path;

h. means for permitting diffusion of gas into and out of the sample chamber; and i. means for detecting the pressure level within the optical waveguide sample chamber.

15. An improved NDIR gas sensor, comprising:

a. a first semiconductor material substrate;

b. a second semiconductor material substrate attached to the first substrate;

c. an optical waveguide formed between the first and second substrates;

d. a light source integrally formed on one of the substrates and positioned at one end of the optical waveguide;

e. a light detector integrally formed on one of the substrates and positioned at the end of the optical waveguide opposite the light source;

f. a bandpass filter interposed in the optical path between the light source and light detector;

g. a first and a second window disposed in the waveguide between the light source and light detector, the first window and second window being micromachined from one of the semiconductor material substrates;

h. a sample chamber interposed between the first and second windows in the optical waveguide, the sample chamber extending along an indirect path between the first and second windows; and i. at least one aperture in the wall of the sample chamber.

16. An improved NDIR gas sensor, comprising:

a. a first silicon substrate;

b. a second silicon substrate attached to the first silicon substrate;

c. an optical waveguide formed between the first and second silicon substrates;

d. a black body light source integrally formed on the first silicon substrate and positioned at one end of the optical waveguide;

e. an infrared light detector integrally formed on the first silicon substrate and positioned at the end of the optical waveguide opposite the light source;

f. a bandpass filter interposed in the optical path between the light source and light detector;

g. a pair of optically transparent silicon windows interposed in the optical path between the light source and light detector so as to define therebetween a sample chamber within the waveguide and thermally isolate the light source and light detector from the sample gas, the sample chamber extending along an indirect path between the light source and light detector;

h. a plurality of apertures in at least one wall of the sample chamber;

i. a gas permeable layer covering the plurality of apertures to prevent particles larger than 0.1 μm from entering the sample chamber;

j. a source driver for energizing the source at a preset frequency; and k. signal processing electronics for converting the electrical output produced by the detector into a signal which represents the concentration of the gas being measured.

17. An improved NDIR gas sensor, comprising:

a. a semiconductor material substrate;

b. an optical waveguide formed within the substrate, the optical waveguide comprising a source chamber, a detector chamber and a sample chamber, the source and detector chambers separated from the sample chamber by a first and a second window, respectively, and the source and detector chambers being located on the same end of the optical waveguide;

c. a light source integrally formed on the substrate in the source chamber;

d. a light detector integrally formed on the substrate in the detector chamber;

e. a bandpass filter interposed in the optical path between the light source and light detector;

f. at least one aperture in a wall of the sample chamber, wherein light from the source is reflected off at least one wall of the sample chamber before reaching the detector.

18. An improved NDIR gas sensor, comprising:

a. a first semiconductor material substrate;

b. a second semiconductor material substrate attached to the first substrate;

c. an optical waveguide formed between the first and second substrates, the optical waveguide comprising a source chamber, a detector chamber and a sample chamber, wherein the source and detector chambers are separated from the sample chamber by a first and second window, respectively, the first window and second window are micromachined from one of the semiconductor material substrates, and the source and detector chambers are located on the same end of the optical waveguide;

d. a light source integrally formed on one of the substrates in the source chamber;

e. a light detector integrally formed on one of the substrates in the detector chamber;

f. a bandpass filter interposed in the optical path between the light source and light detector; and g. at least one aperture in a wall of the sample chamber, wherein light from the source is reflected off at least one wall of the sample chamber before reaching the detector.

* * * * *